(12) United States Patent
Kakehashi

(10) Patent No.: US 9,173,552 B2
(45) Date of Patent: Nov. 3, 2015

(54) ENDOSCOPE

(71) Applicant: OLYMPUS CORPORATION, Tokyo (JP)

(72) Inventor: Taigo Kakehashi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 108 days.

(21) Appl. No.: 13/682,355

(22) Filed: Nov. 20, 2012

(65) Prior Publication Data

US 2013/0150673 A1 Jun. 13, 2013

Related U.S. Application Data

(63) Continuation of application No. PCT/JP2012/062322, filed on May 14, 2012.

(30) Foreign Application Priority Data

May 20, 2011 (JP) ................................. 2011-113903

(51) Int. Cl.
| | | |
|---|---|---|
| A61B 1/00 | (2006.01) | |
| A61B 1/04 | (2006.01) | |
| A61B 1/008 | (2006.01) | |
| A61B 1/005 | (2006.01) | |
| G02B 23/24 | (2006.01) | |
| A61B 1/01 | (2006.01) | |
| A61B 1/018 | (2006.01) | |
| A61B 1/05 | (2006.01) | |
| A61B 1/06 | (2006.01) | |
| A61B 1/07 | (2006.01) | |
| A61B 1/12 | (2006.01) | |
| A61B 17/29 | (2006.01) | |
| A61B 18/12 | (2006.01) | |

(52) U.S. Cl.
CPC ............... *A61B 1/008* (2013.01); *A61B 1/0052* (2013.01); *A61B 1/0055* (2013.01); *A61B 1/0057* (2013.01); *A61B 1/00096* (2013.01); *A61B 1/00114* (2013.01); *A61B 1/01* (2013.01); *A61B 1/018* (2013.01); *A61B 1/05* (2013.01); *A61B 1/0676* (2013.01); *A61B 1/07* (2013.01); *A61B 1/12* (2013.01); *A61B 17/29* (2013.01); *A61B 18/12* (2013.01); *G02B 23/2476* (2013.01)

(58) Field of Classification Search
USPC .......... 600/104, 106, 107, 114–116, 128, 130, 600/139–152; 604/528; 606/1
See application file for complete search history.

(56) References Cited

U.S. PATENT DOCUMENTS 5,381,782 A * 1/1995 DeLaRama et al. ........... 600/149

FOREIGN PATENT DOCUMENTS

JP A-2-118501 5/1990
(Continued)

*Primary Examiner* — Ryan Henderson
(74) *Attorney, Agent, or Firm* — Oliff PLC

(57) ABSTRACT

An endoscope includes an insertion portion including a bending portion configured to bend in four directions, and a flexible tube portion provided so as to be continuous with the bending portion, wherein the bending portion includes a first bending region and a second bending region, and wherein the flexible tube portion comprises inside, four first guide pipes each including a distal end fixed to a distal end of the first bending region and a proximal end fixed to a bending portion operation device, and three second guide pipes each including a distal end fixed to a distal end of the second bending region and a proximal end fixed to a bending portion bent shape switching device.

5 Claims, 7 Drawing Sheets

(56) References Cited

FOREIGN PATENT DOCUMENTS

| JP | A-3-43802 | 2/1991 |
| JP | A-10-328131 | 12/1998 |
| JP | 2008048788 A * | 3/2008 | ............... A61B 1/00 |
| JP | A-2009-112537 | 5/2009 |
| JP | 2010259478 A * | 11/2010 | ............... A61B 1/00 |

* cited by examiner

ENDOSCOPE

CROSS REFERENCE TO RELATED APPLICATION

This application is a continuation application of PCT/JP2012/062322 filed on May 14, 2012 and claims benefit of Japanese Application No. 2011-113903 filed in Japan on May 20, 2011, the entire contents of which are incorporated herein by this reference.

BACKGROUND OF THE INVENTION

1. Field of the Invention

The present invention relates to an endoscope including a bending portion, a bending radius of which can be changed, on a distal end side of an insertion portion.

2. Description of the Related Art

In recent years, endoscopes have widely been used in a medical field and an industrial field. In the case of endoscopes used in the medical field, e.g., an inside of a body can be observed by inserting an insertion portion into the body. Endoscopes are categorized into those of a type whose elongated insertion portion is rigid and those of a type whose elongated insertion portion is flexible.

On the other hand, in the case of endoscopes used in the industrial field, e.g., inspection of whether or not, e.g., damage or corrosion exists can be conducted by inserting a flexible elongated insertion portion into, e.g., a jet engine or a piping in a plant.

Furthermore, in the case of the medical endoscopes, various treatments and the like can be performed by introducing a treatment instrument to the inside of a body via a treatment instrument insertion channel provided in the insertion portion. On the other hand, in the case of the industrial endoscopes, various repairs and the like can be performed by introducing a tool to the inside of an engine through an insertion channel provided in the insertion portion.

In general, an endoscope including a flexible elongated insertion portion includes a bending portion on a distal end side of the insertion portion. The bending portion is configured to bend in a plurality of directions according to operations performed by a user via his/her hand. As described above, with an endoscope including a bending portion, the bending portion is bent to change a direction of observation via an observation optical system provided in a distal end portion of an insertion portion, enabling an inspection for a wide range to be performed.

Furthermore, in the case of an endoscope including a bending portion, when a distal end portion of an insertion portion reaches a flexed part provided in a conduit, the insertion portion can smoothly be inserted toward a deep portion of the conduit by properly bending the bending portion to direct the distal end portion toward the deep portion of the conduit.

A bendable bending portion is mainly configured by aligning a plurality of bending pieces in a longitudinal axis direction and pivotably joining the respective bending pieces so as to bend in, for example, two directions that are upward and downward directions, or four directions that are upward, downward, leftward and rightward directions, and is provided with a plurality of bending wires to respond to the bending directions.

Distal ends of the bending wires are fixed at respective predetermined positions in a distal end bending piece positioned on the distalmost end side from among the bending pieces included in the bending portion. On the other hand, proximal ends of the respective bending wires are fixed at respective predetermined positions in pulleys interlocked with, for example, bending knobs included in a bending operation device provided at an operation portion.

With such configuration, when a user performs an operation to rotate, for example, a bending knob for the upward direction, an upward bending wire from among four bending wires is pulled while a downward bending wire is loosened, whereby the bending portion bends upward.

In this case, the bending portion bends with a predetermined bending radius (also referred to as curvature) from a proximal end of the bending portion in a longitudinal axis direction of the insertion portion as a starting point. In other words, a bending portion configured by aligning a plurality of bending pieces is set to bend with a predetermined bending radius from the proximal end side of the bending portion as a starting point.

Japanese Patent Application Laid-Open Publication No. 2002-345742 discloses an endoscope of a type in which flexibility of a flexible tube portion is adjusted by change in bending stiffness of a coil, the endoscope being a flexibility-variable endoscope that provides enhanced operability and durability of a flexibility adjustment mechanism. The flexibility-variable endoscope includes a wire operation mechanism, which is illustrated in FIG. 2 in Japanese Patent Application Laid-Open Publication No. 2002-345742. The wire operation mechanism, a coil is provided in a flexible tube portion substantially concentrically with the flexible tube portion, a plurality of coil pull wires engaged with the coil are provided at different positions in a circumferential direction of the coil and the plurality of coil pull wires are pulled or loosened to expand/contract the coil. In the flexibility-variable endoscope, flexibility adjustment knobs are operated to pull the coil pull wires to contract the coil, enabling the flexible tube portion to be adjusted from a state in which the flexible tube portion easily bends (soft) to a state in which the flexible tube portion is hard to bend (hard).

SUMMARY OF THE INVENTION

An endoscope according to an aspect of the present invention provides an endoscope including an insertion portion including an observation optical system at a distal end portion disposed at a distal end thereof, a bending portion configured to bend in four directions that are a first direction, a second direction, a third direction and a fourth direction, the bending portion being provided so as to be continuous with a proximal end side of the distal end portion, and a flexible tube portion that is soft and has flexibility, the flexible tube portion being provided so as to be continuous with a proximal end side of the bending portion, a plurality of incorporated components being inserted in the insertion portion, wherein the bending portion comprises a first bending region including a plurality of bending pieces pivotably joined so that the first bending region bends in the four directions, the plurality of bending pieces being included in a distal end side of the bending portion, and a second bending region provided so as to be continuous with a proximal end side of the first bending region, the second bending region including a plurality of bending pieces pivotably joined so that the second bending region bends in the four directions, the plurality of bending pieces being included in the proximal end side of the bending portion; and wherein the flexible tube portion comprises inside, four first guide pipes disposed at respective positions in an inner circumferential face of the flexible tube portion, the positions corresponding to the four directions that are bending directions of the bending portion, the four first guide pipes allowing four bending wires corresponding to the bending directions of the bending portion to be inserted therethrough so that the respective bending wires freely advance/retract, the four first guide pipes each including a distal end fixed to a distal end of the first bending region and a proximal end fixed to a bending portion operation device provided at an operation portion provided so as to be continuous with a proximal end side of the insertion portion, and three second guide pipes disposed at predetermined positions at the inner circumferential face of the flexible tube portion, the three second guide pipes allowing three bent shape switching wires to be inserted therethrough so that the respective bent shape switching wires freely advance/retract, the three second guide pipes each including a distal end fixed to a distal end of the second bending region and a proximal end fixed to a bending portion bent shape switching device provided at the operation portion.

BRIEF DESCRIPTION OF THE DRAWINGS

FIG. 1 is a diagram illustrating an endoscope.

FIG. 2 is a cross-sectional view in a longitudinal direction of an insertion portion, which illustrates bending wires and a bent shape switching wire inserted in the inside of the insertion portion of an endoscope.

FIG. 3 is a cross-sectional diagram along line Y3-Y3 of FIG. 2.

FIG. 4 is a cross-sectional diagram along line Y4-Y4 of FIG. 2.

FIG. 5 is a cross-sectional diagram along line Y5-Y5 of FIG. 2.

FIG. 6 is a diagram illustrating a bending portion bent in association with a pull of a bending wire when no bent shape switching wires are pulled.

FIG. 7 is a diagram illustrating a configuration of a bending portion bent shape switching device provided in an operation portion.

FIG. 8 is a diagram illustrating a bending portion bent as a result of a bending wire being pulled when bent shape switching wires are pulled.

FIG. 9 is a diagram illustrating an operation portion including a lever for pulling bent shape switching wires.

FIG. 10 is a diagram illustrating a link mechanism provided in an operation portion, the link mechanism pulling/loosening bent shape switching wires in association with operation of a lever; and FIG. 11 is a cross-sectional diagram along line Y11-Y11 in FIG. 10.

DETAILED DESCRIPTION OF THE PREFERRED EMBODIMENT

An embodiment of the present invention will be described below with reference to FIGS. 1 to 8.

Figure 1:
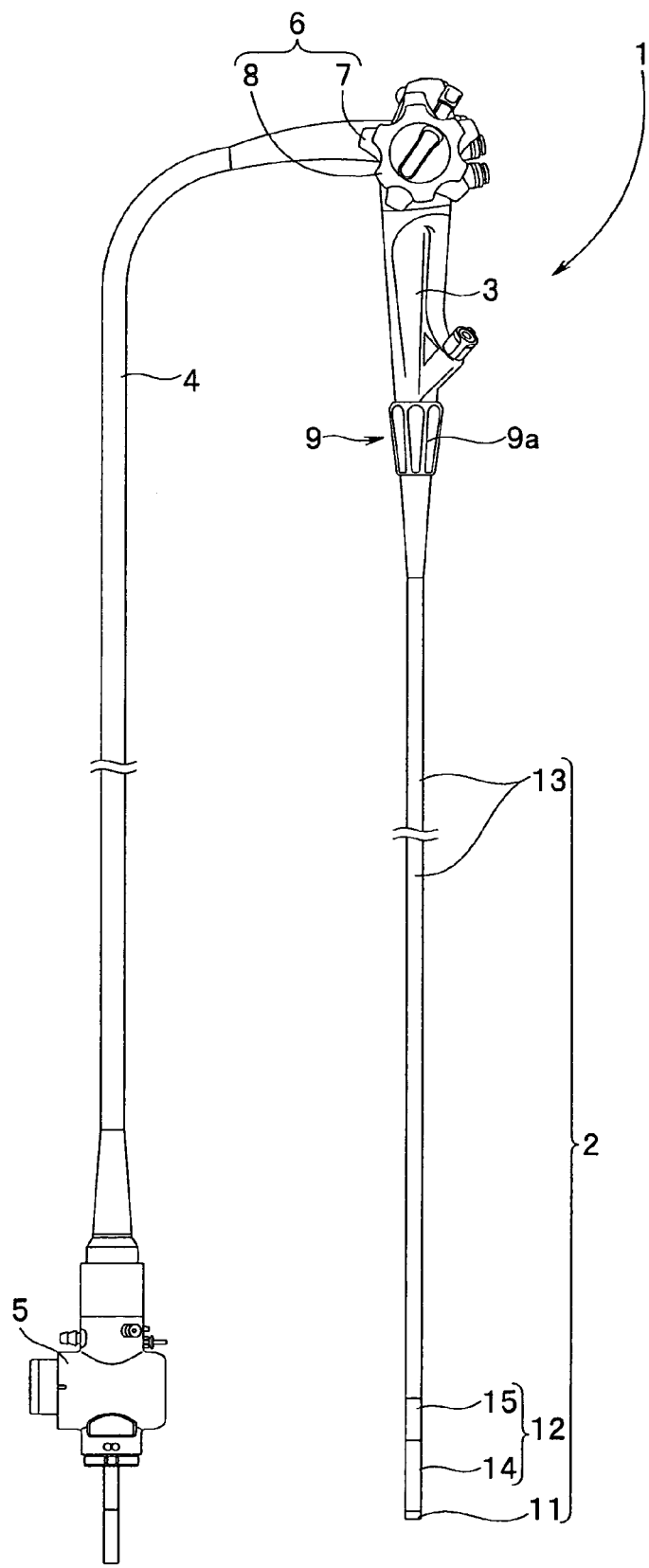
FIGS. 1 to 8 relate to an embodiment of the present invention.

As illustrated in FIG. 1, an endoscope 1 includes an insertion portion 2, an operation portion 3 and a universal cord 4. The universal cord 4 extends out from a side portion of the operation portion 3, and is provided with a connector 5 at an end of the extension thereof. The connector 5 is electrically connected to external apparatuses such as a control apparatus and an illumination apparatus.

In the present embodiment, the operation portion 3 is mainly provided with a bending portion operation device 6 and a bending portion bent shape switching device (hereinafter abbreviated as bent shape switching device) 9. The bent shape switching device 9 includes an operation ring 9a that rotates around an axis of the insertion portion 2.

The bending portion operation device 6 is a device for performing an operation to bend a bending portion included in the insertion portion 2 (see reference numeral 12, which will be described later). In the present embodiment, the bending portion operation device 6 includes an upward/downward bending operation knob (hereinafter abbreviated as upward/downward knob) 7 and a leftward/rightward bending operation knob (hereinafter abbreviated as leftward/rightward knob) 8. The upward/downward knob 7 and the leftward/rightward knob 8 are pivotable around a non-illustrated axis, and in FIG. 1, rotate clockwise or counterclockwise.

Figure 2:
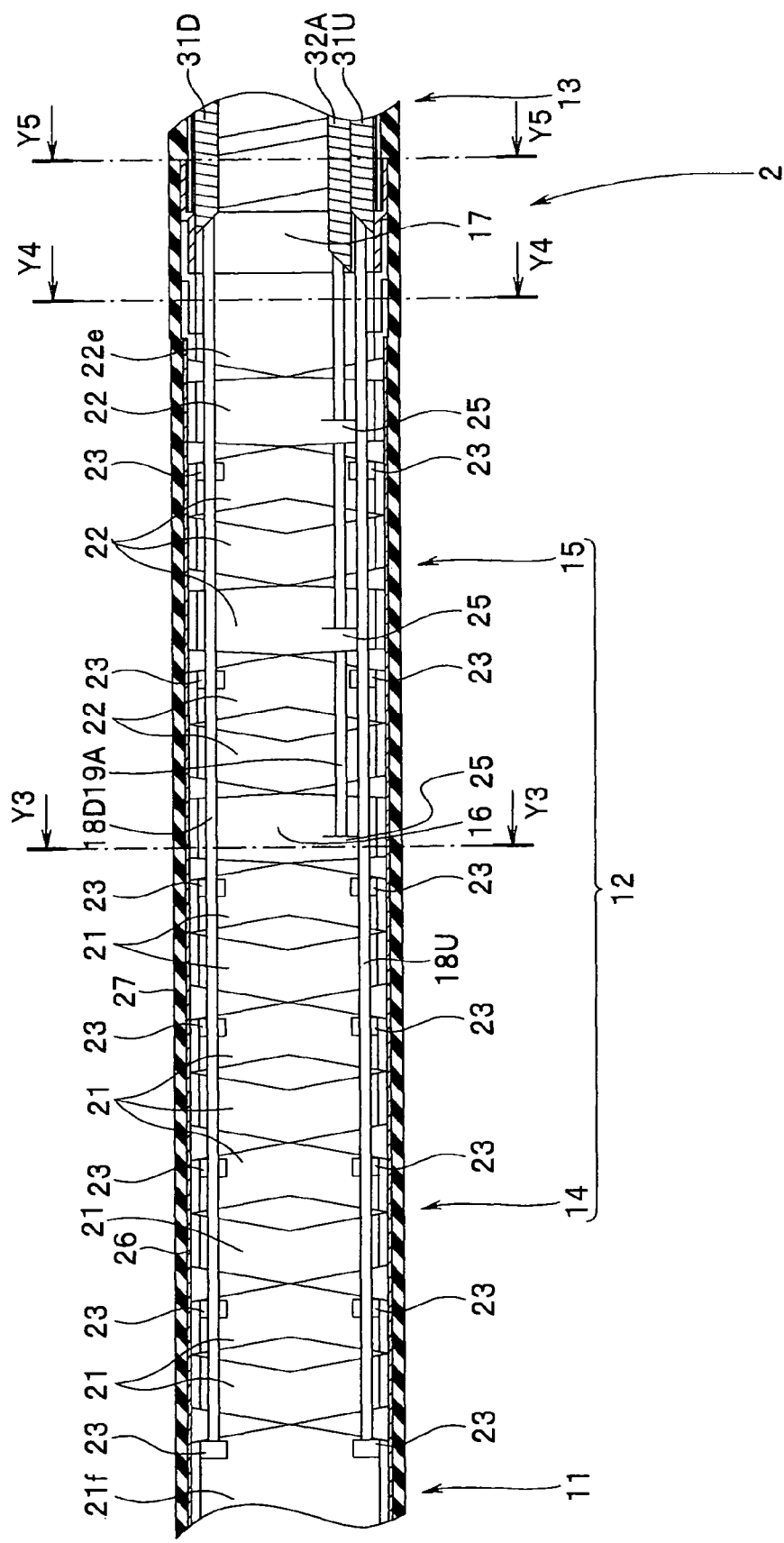

As illustrated in FIGS. 1 and 2, the insertion portion 2 includes a distal end portion 11, a bending portion 12 and a flexible tube portion 13 provided continuously in this order from the distal end side. The operation portion 3 is provided so as to be continuous with the proximal end side of the insertion portion 2.

The distal end portion 11 is provided with an observation optical system. The observation optical system includes a non-illustrated illumination unit that illuminates a site to be observed and an image pickup unit (not illustrated) that picks up an image of the site to be observed, which is illuminated by the illumination unit.

The bending portion 12 according to the present embodiment includes a first bending region 14, a second bending region 15 and a joint piece 16. In other words, the bending portion 12 is divided in two regions that are the first bending region 14 and the second bending region 15. The first bending region 14 provides the distal end side of the bending portion 12. The second bending region 15 is provided so as to be continuous with the proximal end side of the first bending region 14 and provides the proximal end side of the bending portion 12. The first bending region 14 is formed by pivotably joining, e.g., a plurality of bending pieces 21 so as to bend in four directions that are upward, downward, leftward and rightward directions. Furthermore, the second bending region 15 is formed by pivotably joining, e.g., a plurality of bending pieces 22 so as to bend in four directions that are upward, downward, leftward and rightward directions. The bending pieces 21 included in the first bending region 14 and the bending pieces 22 included in the second bending region 15 may each have a same configuration or different configurations.

The first bending region 14 includes a distal end bending piece 21*f*, the plurality of bending pieces 21 and the joint piece 16, which are pivotably jointed together, so as to bend in four directions that are upward, downward, leftward and rightward directions. The distal end bending piece 21*f* provides a distalmost end of the bending portion 12 and a distal end of the first bending region. The joint piece 16 provides a proximal end of the first bending region.

On the other hand, the second bending region 15 includes the joint piece 16, the plurality of bending pieces 22, and a proximal end bending piece 22*e*, which are pivotably jointed together, so as to bend in four directions that are upward, downward, leftward and rightward directions. The joint piece 16 provides a distal end of the second bending region. The proximal end bending piece 22*e* provides a proximalmost end of the bending portion 12 and a proximal end of the second bending region.

In such configuration, the joint piece 16 serves as both a proximal end bending piece of the first bending region 14 and a distal end bending piece of the second bending region 15.

The flexible tube portion 13 is soft and has flexibility. The proximal end bending piece 22e is joined to a joint tube sleeve 17 fixedly provided on the distal end of the flexible tube portion 13.

As illustrated in FIGS. 2 to 5, inside the insertion portion 2, four bending wires 18 for bending the bending portion 12 in four directions that are upward, downward, leftward and rightward directions, three bent shape switching wires 19, which will be described later, an image pickup cable 33, two light guides 34 and 35, a treatment instrument insertion channel tube (hereinafter abbreviated as treatment instrument channel) 36 and an air/water feeding tube 37 are inserted.

The four bending wires 18 are inserted inside four first guide pipes 31 so as to freely advance/retract, respectively. The four first guide pipes 31 correspond to the respective bending directions. Furthermore, the three bent shape switching wires 19 are respectively inserted inside three second guide pipes 32, which will be described later, so as to freely advance/retract.

Note that in FIG. 2, the image pickup cable 33, the light guides 34 and 35, the treatment instrument channel 36, and the air/water feeding tube 37 are not illustrated for simplification of the drawing. Furthermore, from among the four bending wires 18, two bending wires 18 are illustrated, and from among the three bent shape switching wires 19, one bent shape switching wire is illustrated.

Figure 3:
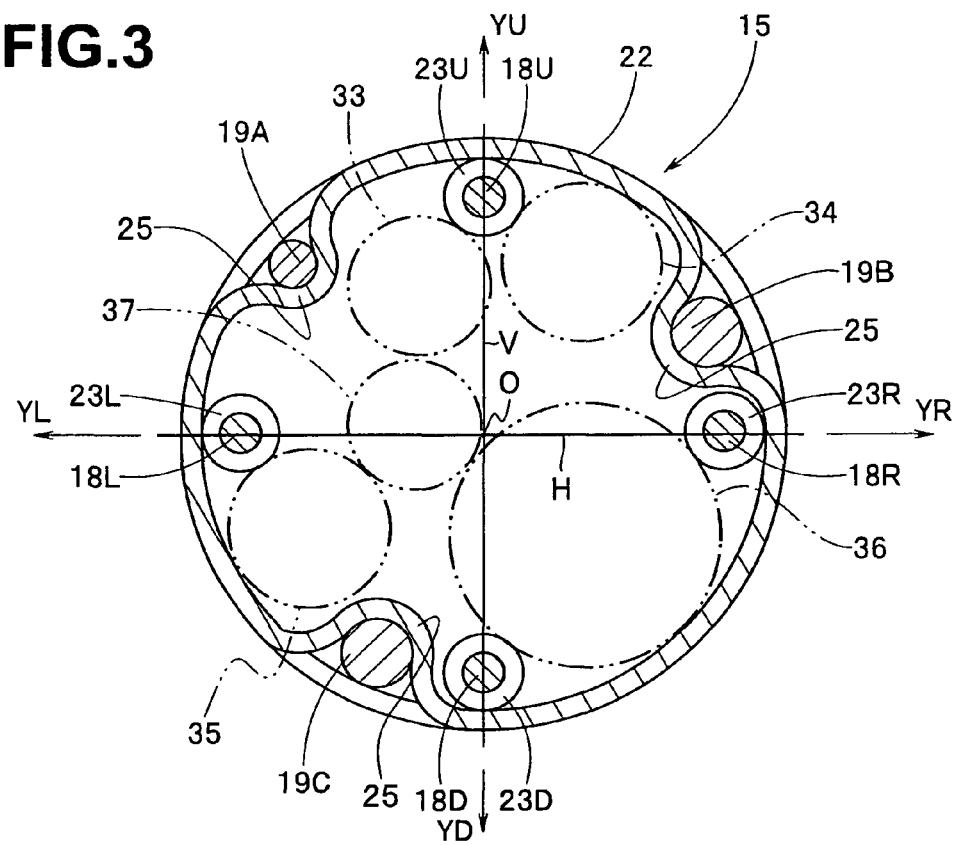
Figure 4:
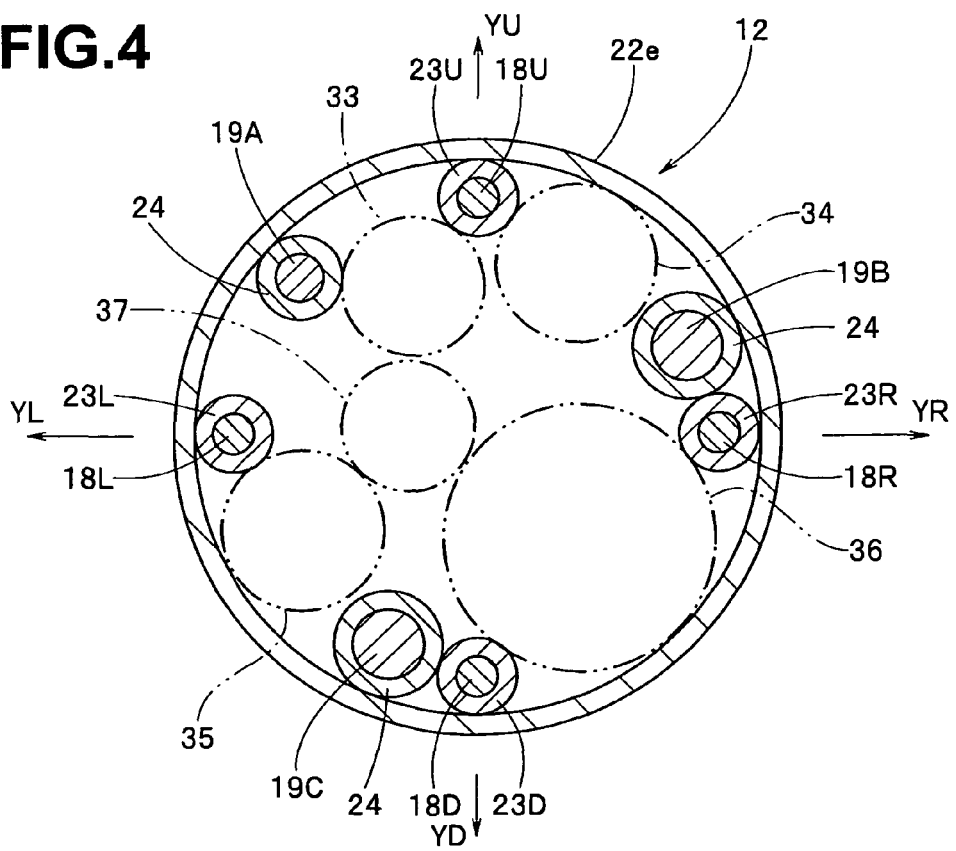
Figure 5:
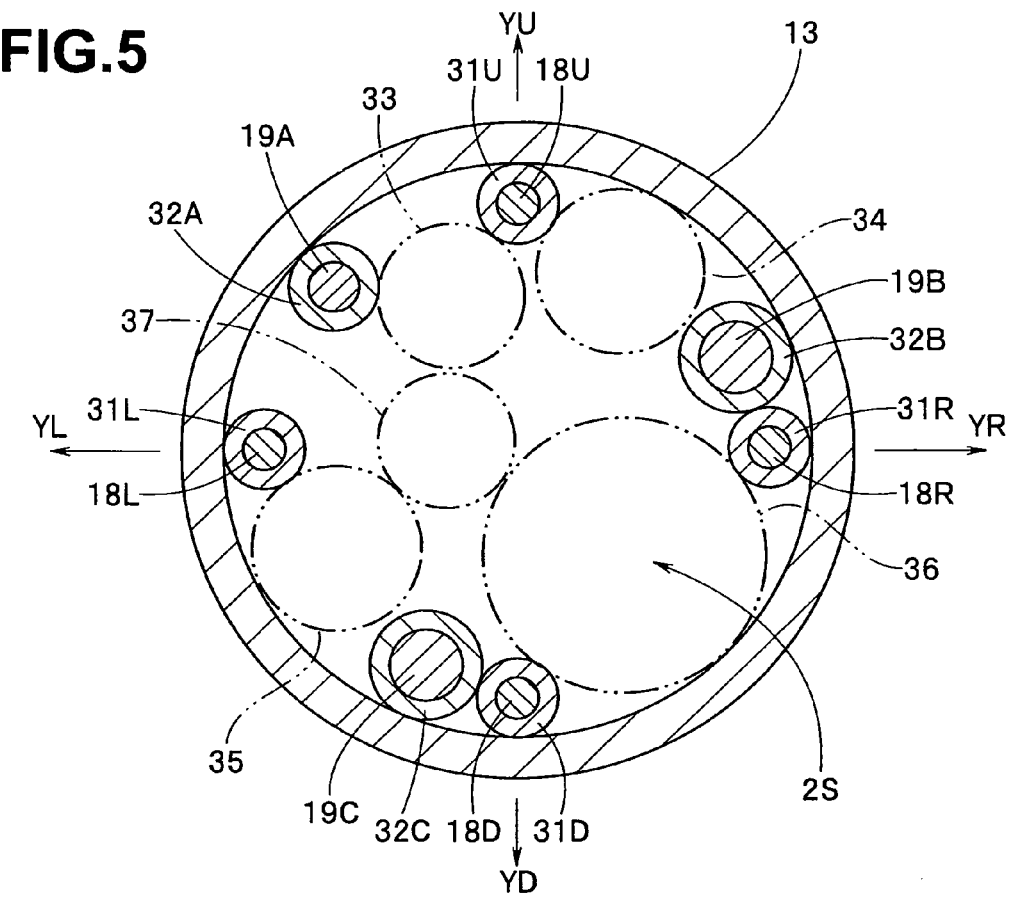

Furthermore, in FIGS. 3 to 5, the image pickup cable 33, the light guides 34 and 35, the treatment instrument channel 36 and the air/water feeding tube 37 are incorporated components inserted in the insertion portion 2, which are indicated by alternate long and two short dashes lines.

The treatment instrument channel 36 is a conduit for introducing a treatment instrument such as grasping forceps or an electronic surgical knife into, for example, a body. The treatment instrument channel 36 desirably has a large inner diameter dimension. In the present embodiment, the treatment instrument channel 36 is an incorporated component having a largest outer diameter.

As illustrated in FIGS. 2 and 5, the four first guide pipes 31 are disposed at respective positions corresponding to the four bending directions of the bending portion 12, which are predetermined positions in an inner circumferential face of the flexible tube portion 13. More specifically, the four first guide pipes 31 are provided at predetermined intervals, for example, regular intervals, in a circumferential direction in the inner circumferential face of the flexible tube portion 13.

Respective distal ends of the four first guide pipes 31 are fixed at respective predetermined positions in the joint sleeve 17, and respective proximal ends of the four first guide pipes 31 are fixed at non-illustrated predetermined positions inside the operation portion 3.

The respective bending wires 18 are inserted inside the first guide pipe 31. Respective distal ends of the bending wires 18 extend out from respective distal end openings of the first guide pipes 31 into the bending portion 12, and are fixed at respective predetermined positions in the distal end bending piece 21f by means of, for example, brazing. More specifically, the respective distal ends of the bending wires 18 are fixed at respective positions corresponding to the four directions that are upward, downward, leftward and rightward direction in the bending portion 12.

On the other hand, respective proximal ends of the bending wire 18 extend out from respective proximal end openings of the first guide pipes 31 into the operation portion 3, and are fixed at predetermined positions in a non-illustrated upward/downward pulley included in the bending portion operation device 6, and predetermined positions in a non-illustrated leftward/rightward pulley. The upward/downward pulley is configured integrally with the upward/downward knob 7, and the left/right pulley is configured integrally with the leftward/rightward knob 8.

In FIGS. 3 to 5, the arrow YU direction indicates a first direction (upward direction), which is one of the bending directions of the bending portion 12, the arrow YD direction indicates a second direction (downward direction), which is opposite to the upward direction and is one of the bending directions of the bending portion 12. In FIGS. 3 to 5, the arrow YL direction indicates a third direction (leftward direction), which is one of the bending direction of the bending portion 12, and the arrow YR direction indicates a fourth direction (rightward direction), which is opposite to leftward and is one of the bending directions of the bending portion 12.

In addition, reference numeral 31U indicates an upward first guide pipe, reference numeral 31D indicates a downward first guide pipe, reference numeral 31L indicates a leftward first guide pipe, and reference numeral 31R indicates a rightward first guide pipe. Furthermore, reference numeral 18U indicates an upward bending wire, reference numeral 18D indicates a downward bending wire, reference numeral 18L indicates a leftward bending wire, and reference numeral 18R indicates a rightward bending wire.

Note that reference numeral 23 in FIG. 2 denotes a bending wire support. The bending wire supports 23 are fixedly provided at predetermined positions in inner faces of the respective bending pieces 21 and 22 in order to define positions in a circumferential direction and positions in a radial direction of the respective bending wires 18U, 18D, 18L and 18R inside the bending portion 12.

Figure 6:
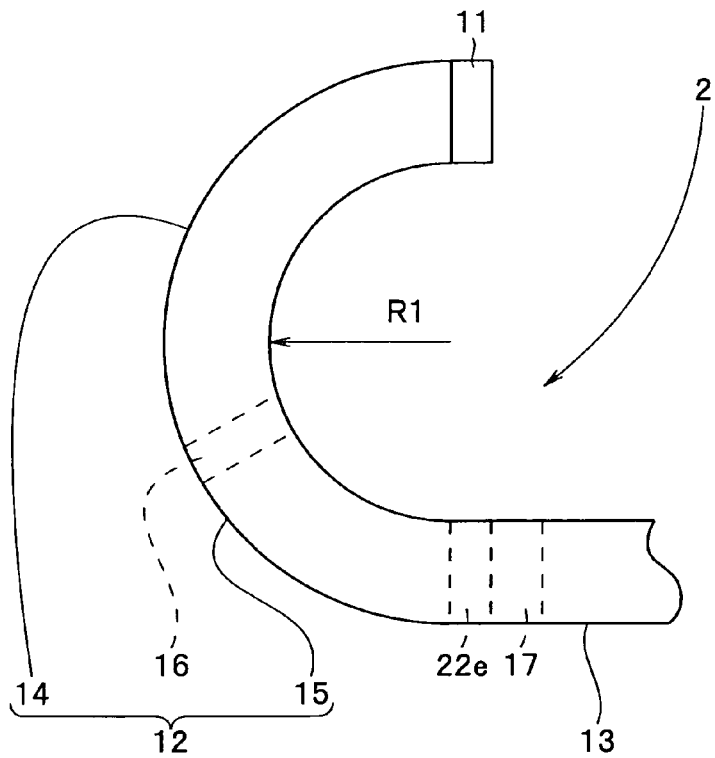

When the later-described bent shape switching wires are not pulled, if, for example, the upward bending wire 18U is pulled by operation of the upward/downward knob 7, the bending portion 12 of the endoscope 1 according to the present embodiment bends upward with a predetermined bending radius R1, as illustrated in FIG. 6. In such bending state, the downward bending wire 18D is in a loosened state. The bending portion 12 bends from the proximal end bending piece 22e, which provides the proximalmost end, as a starting point. Conversely, if the downward bending wire 18D is pulled by operation of the upward/downward knob 7, the bending portion 12 bends downward with the bending radius R1 from the proximal end bending piece 22e as a starting point. In such bending state, the upward bending wire 18U is in a loosened state.

On the other hand, when the bent shape switching wires are not pulled, if, for example, the leftward bending wire 18L is pulled by operation of the leftward/rightward knob 8, the bending portion 12 of the endoscope 1 bends leftward with the bending radius R1 from the proximal end bending piece 22e as a starting point. In such bending state, the rightward bending wire 18R is in a loosened state. Conversely, if the rightward bending wire 18R is pulled by operation of the leftward/rightward knob 8, the bending portion 12 bends rightward with the bending radius R1 from the proximal end bending piece 22e as a starting point. In such bending state, the leftward bending wire 18L is in a loosened state.

In other words, when the later-described bent shape switching wires are not pulled, in the bending portion 12, in association with operation of the upward/downward knob 7 or the leftward/rightward knob 8, the second bending region 15 and the first bending region 14 included in the bending portion 12 integrally bend in any direction of the upward, downward, leftward and rightward directions.

As illustrated in FIGS. 2 and 5, the three second guide pipes 32 are arranged in the inner circumferential face of the flexible tube portion 13 in consideration of insertion positions of a plurality of incorporated components inserted inside the insertion portion 2. More specifically, positions in a circumferential direction where the three second guide pipes 32 are arranged are determined in light of a position where the treatment instrument channel 36 having a largest outer diameter from among those of the incorporated components is arranged.

More specifically, two of the three second guide pipes 32 are arranged so as to provide a broadest largest incorporated component insertion space 2S for arranging the treatment instrument channel 36 inside the insertion portion 2. In other words, a second guide pipe 32, which is one of the two second guide pipes 32, is arranged on the YU side of the rightward first guide pipe 31R so as to be in contact with an outer circumferential face of the rightward first guide pipe 31R. On the other hand, a second guide pipe 32, which is the other of the second guide pipes 32, is arranged on the YL side of the downward first guide pipe 31D so as to be in contact with an outer circumferential face of the downward first guide pipe 31D. As a result, the largest incorporated component insertion space 2S for arranging the treatment instrument channel 36 is formed between the rightward first guide pipe 31R and the downward first guide pipe 31D.

Then, the remaining one of the three second guide pipes 32 is arranged in the inside of the leftward first guide pipe 31L and the upward first guide pipe 31U. More specifically, the remaining one second guide pipe 32 is arranged at a position facing the treatment instrument channel 36 arranged between the rightward first guide pipe 31R and the downward first guide pipe 31D.

Respective distal ends of the three second guide pipes 32 are fixed at respective predetermined positions in the joint sleeve 17, and respective proximal ends of the three second guide pipes 32 are fixed at non-illustrated predetermined positions inside the operation portion 3.

The respective bent shape switching wires 19 are inserted through the respective second guide pipes 32. Respective distal ends of the bent shape switching wires 19 extend out from respective distal end openings of the second guide pipes 32 into the bending portion 12, and are fixed at predetermined positions in the joint piece 16 by means of, for example, brazing. On the other hand, respective proximal ends of the bent shape switching wires 19 extend out from proximal ends of the second guide pipes 32 into the operation portion 3, and are fixed at predetermined positions in the bent shape switching device 9.

The respective bent shape switching wires 19 inserted through the second guide pipes 32 have different tensile strengths. Thus, in the present embodiment, reference numerals 19A, 19B and 19C are provided to the bent shape switching wires to distinguish the respective bent shape switching wires from one another.

In the present embodiment, tensile strengths of bent shape switching wires 19B and 19C are set in advance to be larger than a tensile strength of a bent shape switching wire 19A, and one bent shape switching wire 19B and one bent shape switching wire 19C each have a tensile strength that enables a hardened state of the second bending region 15, which will be described later, to be kept.

In the present embodiment, where the bent shape switching wire 19A, and the bent shape switching wires 19B and 19C include a same material, the bent shape switching wire 19A, and the bent shape switching wires 19B and 19C have different diameter dimensions. Then, the respective diameters of the bent shape switching wires 19B and 19C are each set to be larger than the diameter of the bent shape switching wire 19A to set a large tensile strength.

Since the diameter dimensions of the bent shape switching wires 19A, 19B and 19C are different from one another, reference numerals 32A, 32B and 32C are provided to the three second guide pipes 32, respectively, to distinguish the three second guide pipes 32 from one another. In other words, the bent shape switching wire 19C is inserted through the second guide pipe 32C, the bent shape switching wire 19B is inserted through the second guide pipe 32B, and the bent shape switching wire 19A is inserted through the second guide pipe 32A.

Note that the tensile strengths of the bent shape switching wires may be made to be different from one another using bent shape switching wires having different Young's moduli without the wire diameters being made to be different from one another. Furthermore, the bent shape switching wire 19A is set to have a predetermined tensile strength or larger. More specifically, the tensile strengths are ones enabling a hardened state of the second bending region 15 to be kept by the two bent shape switching wires 19A and 19C and enabling a hardened state of the second bending region 15 to be kept by the two bent shape switching wires 19A and 19B.

Here, the bent shape switching device 9 in which the proximal ends of the bent shape switching wires 19A, 19B and 19C are arranged will be described.

Figure 7:
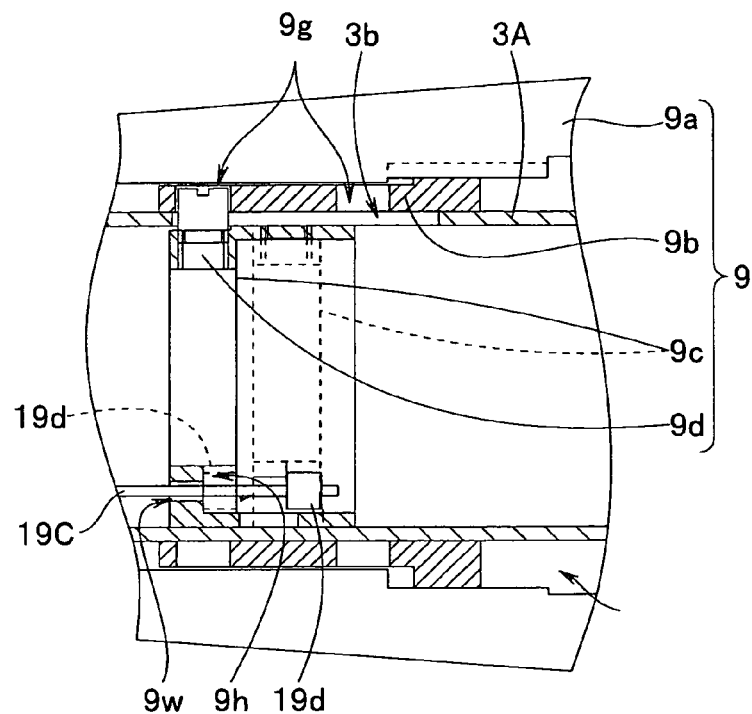

As illustrated in FIG. 7, the bent shape switching device 9 mainly includes an operation ring 9a, a cam ring 9b, a moving ring 9c and a cam pin 9d. A stopper 19d is fixedly provided in advance at the proximal end of each of the bent shape switching wires 19A, 19B and 19C.

Note that FIG. 7 illustrates one of the three bent shape switching wires 19A, 19B and 19C for simplification of the drawing.

The operation ring 9a is configured so as to pivot around a longitudinal axis of the operation portion at a predetermined position on the outer circumferential face side of a distal end portion 3A of the operation portion. In other words, the operation ring 9a is grasped by a user to rotate the operation ring 9a clockwise or counterclockwise around the longitudinal axis.

The cam ring 9b is arranged on an inner circumferential face of the operation ring 9a, and is slidably arranged on the outer circumferential face of the distal end portion 3A of the operation portion. The cam ring 9b is configured so as to advance/retract the operation portion 3 in the longitudinal direction in association with rotation of the operation ring 9a. In the cam ring 9b, a groove cam 9g having a predetermined shape are formed.

The moving ring 9c is arranged so as to slide inside the operation portion 3. More specifically, the moving ring 9c is arranged so as to slide on the inner circumferential face side of the cam ring 9b inside the distal end portion 3A of the operation portion. At a predetermined position in the moving ring 9c, a cam pin 9d that projects toward the outer circumference is fixedly provided. An projection end portion of the cam pin 9d passes through a long hole 3b formed in advance in the distal end portion 3A of the operation portion and is arranged inside the groove cam 9g of the cam ring 9b.

Reference numeral 9h is a stopper receiving hole that receives a stopper 19d. A stopper receiving hole 9h is formed at a predetermined position in a proximal end face of the moving ring 9c in order to define a position in the circumferential direction of the proximal end portion of each of the bent shape switching wires 19A, 19B and 19C. Reference numeral 9w denotes an axial through hole through which a bent shape switching wire is inserted. A center axis of the stopper receiving hole 9h and a center axis of the axial through hole 9w are coaxial to each other.

With such configuration, when the operation ring 9a is rotated, for example, clockwise, the cam ring 9b moves toward the proximal end side in the longitudinal direction of the operation portion 3 in association with the rotation. In association with the movement of the cam ring 9b, the cam pin 9d moves inside the groove cam 9g, and in association with the movement of the pin 9d, the moving ring 9c moves toward the proximal end side in the longitudinal direction of the operation portion 3. As a result, the moving ring 9c retracts from the position indicated by solid lines to the position indicated by dashed lines. Accordingly, the respective stoppers 19d fixedly provided at the proximal ends of the bent shape switching wires 19A, 19B and 19C simultaneously retract as indicated by solid lines.

In association with the retraction of the respective stoppers 19d, tensile forces of the bent shape switching wires 19A, 19B and 19C increase simultaneously. In the present embodiment, the distal ends of the bent shape switching wires 19A, 19B and 19C are fixed to the joint piece 16, which is a distal end bending piece in the second bending region 15. Thus, when the bent shape switching wires 19A, 19B and 19C are pulled, the tensile forces of the wires 19A, 19B and 19C increase simultaneously, whereby the bent shape switching wires 19A, 19B and 19C become tense. Then, the plurality of bending pieces 22 included in the second bending region 15 contract in the axial direction of the insertion portion. As a result, the second bending region 15 changes from a bendable state to a hardened state.

When the second bending region 15 is in a hardened state, the first bending region 14 included in the bending portion 12 in the present embodiment is in a bendable state.

In the present embodiment, the second bending region 15 is made to enter a hardened state by operation of the bent shape switching device 9 in the endoscope 1 and, for example, the upward bending wire 18U is pulled by operation of the upward/downward knob 7. Then, the first bending region 14 of the bending portion 12 bends upward from the joint piece 16, which provides the proximalmost end of the first bending region 14, as a starting point.

As illustrated in FIG. 3, the bent shape switching wire 19C is arranged at a position substantially facing the upward bending wire 18U, in other words, is arranged at a position where the bent shape switching wire 19C and the upward bending wire 18U are substantially symmetric to each other with respect to a center point O, namely, the upward bending wire 18U is arranged at a position shifted by almost 180 degrees from the wire 19C in the circumferential direction. With such configuration, when the second bending region 15 is in a hardened state, if the first bending region 14 is bent upward, a large tensile force is imposed on the bent shape switching wire 19C arranged in a lower space of the insertion portion compared to the bent shape switching wires 19A and 19B arranged in an upper space of the insertion portion, the lower space and the upper space resulting from dividing the insertion portion by a horizontal line H running through the center point O.

Figure 8:
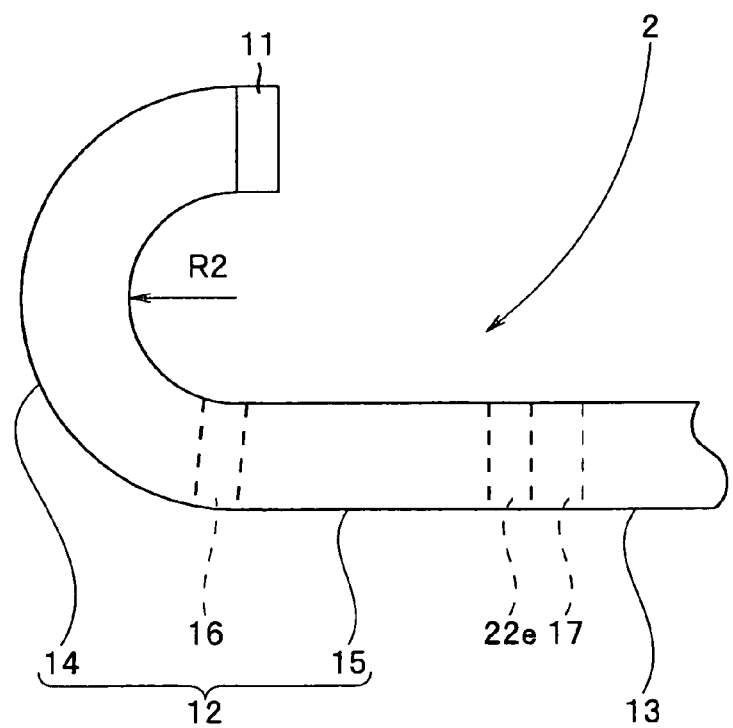

However, as described above, the tensile strength of the bent shape switching wire 19C is set so that the hardened state of the second bending region 15 can be kept. Accordingly, one bent shape switching wire 19C keeps the hardened state of the second bending region 15, and only the first bending region 14 bends upward. As a result, as illustrated in FIG. 8, the first bending region 14 of the bending portion 12 bends upward with a predetermined bending radius R2 that is smaller than the bending radius R1.

On the other hand, in the present embodiment, as described above, when the second bending region 15 is made to enter a hardened state by operation of the bent shape switching device 9 and, for example, the leftward bending wire 18L is pulled by operation of the leftward/rightward knob 8, the first bending region 14 bends leftward with the bending radius R2 from the joint piece 16 as a starting point.

In such bending state, as illustrated in FIG. 3, the bent shape switching wire 19B is arranged at a position substantially facing the leftward bending wire 18L. Thus, when the first bending region 14 bends leftward, a large tensile force is imposed on the bent shape switching wire 19B arranged in a right space of the insertion portion compared to the bent shape switching wires 19A and 19C arranged in a left space of the insertion portion, the right space and the left space resulting from dividing the insertion portion by a vertical line V perpendicular to the horizontal line H and running through the center point O.

In such case, the tensile strength of the bent shape switching wire 19B is set so that the hardened state of the second bending region 15 can be kept. Accordingly, one bent shape switching wire 19B keeps the hardened state of the second bending region 15, and only the first bending region 14 bends leftward. As a result, as illustrated in FIG. 8, the first bending region 14 of the bending portion 12 bends leftward with the bending radius R2.

Note that when the second bending region 15 is in a hardened state, if the downward bending wire 18D is pulled by operation of the upward/downward knob 7 in such a manner opposite to the above, the first bending region 14 bends downward with the bending radius R2 from the joint piece 16 as a starting point.

Then, a large tensile force is imposed on the two bent shape switching wires 19A and 19B arranged inside the upward space compared to the bent shape switching wire 19C arranged inside the downward space, the upward space and the downward space resulting from the division by the horizontal line H in FIG. 3.

In such case, the hardened state of the second bending region 15 is kept by the two bent shape switching wires 19A and 19B arranged inside the upward space, and only the first bending region 14 bends downward. As a result, the bending portion 12 bends downward with the bending radius R2.

On the other hand, when the second bending region 15 is in a hardened state, if the rightward bending wire 18R is pulled by operation of the leftward/rightward knob 8 in such a manner opposite to the above, the first bending region 14 bends rightward from the joint piece 16 as a starting point.

Then, a large tensile force is imposed on the two bent shape switching wires 19A and 19C arranged in the left space compared to the bent shape switching wire 19B arranged in the right space, the left space and the right space resulting from the division by the vertical line V in FIG. 3.

In such case, since the hardened state of the second bending region 15 is kept by the two bent shape switching wires 19A and 19C arranged in the left space, only the first bending region 14 bends rightward. As a result, the bending portion 12 bends rightward with the bending radius R2.

In other words, in the bending portion 12, when the second bending region 15 is in a hardened state, only the first bending region 14 included in the bending portion 12 bends either upward or downward with the bending radius R2 in association with operation of the upward/downward knob 7, and only the first bending region 14 included in the bending portion 12 bends either leftward or rightward with the bending radius R2 in association with operation of the leftward/rightward knob 8.

Note that in the above-described embodiment, the illumination unit includes two light guides 34 and 35. However, the illumination unit are not limited to one including two light guides 34 and 35, and the illumination unit may include one light guide or three or more light guides. Furthermore, the illumination unit is not limited to one including light guides, and may include light-emitting elements such as LEDs. In the case of light-emitting elements, electric wires extending out from the light emitting elements are incorporated components.

Furthermore, in the above-described embodiment, a position where the treatment instrument channel 36 is arranged is between the rightward first guide pipe 31R and the downward first guide pipe 31D. However, the position where the treatment instrument channel 36 is arranged is not limited to a position between the rightward first guide pipe 31R and the downward first guide pipe 31D. In other words, the position may be between the downward first guide pipe 31D and the leftward first guide pipe 31L, or between the leftward first guide pipe 31L and the upward first guide pipe 31U, or between the upward first guide pipe 31U and the rightward first guide pipe 31R as long as such first guide pipes are first guide pipes adjacent to each other from among the first guide pipes 31U, 31R, 31D and 31L.

Furthermore, the endoscope is not limited to one having a configuration including the treatment instrument channel 36 as an incorporated component, and may be one having a configuration eliminating the need to provide a treatment instrument insertion channel.

A bent shape switching wire support 24 is provided at a predetermined position in the inner face of each bending piece 22 in order to define a position in the circumferential direction and a position in the radial direction of each of the bent shape switching wires 19A, 19B and 19C inside the second bending region 15. The position of each of the bent shape switching wires 19A, 19B and 19C may be defined by a string guide (see reference numeral 25 in FIG. 3) instead of the bent shape switching wire supports 24. Note that diameter dimensions of the bent shape switching wire supports 24 also correspond to the diameter dimensions of the bent shape switching wires 19A, 19B and 19C as with the diameter dimensions of the second guide pipes 32.

Furthermore, reference numeral 26 in FIG. 2 denotes a braiding. The braiding 26 covers an outer circumference of the first bending region 14 and an outer circumference of the second bending region 15. Reference numeral 27 denotes a bending rubber. The bending rubber 27 covers an outer circumference of the braiding 26.

Furthermore, the following relationship is set for the tensile strengths of the three bent shape switching wires 19A, 19B and 19C.

Tensile strength of bent shape switching wire 19B>Tensile strength of bent shape switching wire 19A Tensile strength of bent shape switching wire 19C>Tensile strength of bent shape switching wire 19A Tensile strength of bent shape switching wire 19C≥Tensile strength of bent shape switching wire 19B Setting the tensile strengths of the bent shape switching wires as described above enables a capability of upward bending, for which a bending angle is set to be largest in general and for which a bending operation is most frequently performed, to be reliably kept for a long period of time.

Furthermore, as a result of the operation ring 9a being rotated in the opposite direction when the second bending region 15 is hardened, the tensile forces of the bent shape switching wires 19A, 19B and 19C decrease simultaneously. As a result, the second bending region 15 recovers from the hardened state to a bendable state.

As described above, the bending portion 12 of the endoscope 1 is divided into two regions, that is, the first bending region 14 and the second bending region 15. Then, at the operation portion 3 of the endoscope 1, the upward/downward knob 7 for performing an operation to bend the bending portion 12 upward/downward, the leftward/rightward knob 8 for performing an operation to bend the bending portion leftward/rightward and a bent shape switching device 9 for changing the second bending region 15 into a hardened state are provided. Furthermore, the distal ends of the bending wires 18 corresponding to upward, downward, leftward and rightward directions, which are each pulled/loosened via the upward/downward knob 7 or the leftward/rightward knob 8 of the endoscope 1, are fixed at the distal end bending piece 21f that provides the distalmost end of the bending portion 12. On the other hand, the distal ends of the three bent shape switching wires 19 that are pulled/loosened by the bent shape switching device 9 in the endoscope 1 are fixed to the joint piece 16 that joins the first bending region 14 and the second bending region 15 to each other and provides the proximalmost end of the first bending region 14.

According to the endoscope 1 configured as described above, after the second bending region 15 is hardened by operation of the bent shape switching device 9, only the first bending region 14 included in the bending portion 12 can be bent either upward or downward or either leftward or rightward with the bending radius R2 by operating the upward/downward knob 7 or the leftward/rightward knob 8.

On the other hand, without operating the bent shape switching device 9, that is, when the second bending region 15 is in a bendable state, the first bending region 14 and the second bending region 15 included in the bending portion 12 can simultaneously be bent either upward or downward or either leftward or rightward with the bending radius R1 that is larger than the bending radius R2 by operating the upward/downward knob 7 or the leftward/rightward knob 8.

As a result, a user can obtain optimum operability and optimum observation performance by selectively switching the bending radius of the bending portion between the bending radius R1 and the bending radius R2 considering, e.g., a size of a space of a site to be observed in advance, by an operation performed via his/her hand.

Furthermore, a worker can arrange the treatment instrument channel 36, which is a component incorporated in the endoscope, the component having a largest diameter dimension, between the first guide pipes 31R and 31D and easily arrange, e.g., the image pickup cable 33, the light guides 34 and 35, and the air/water feeding tube 37, which are incorporated components each having a diameter smaller than that of the component incorporated in the endoscope, the component having a largest diameter, inside the insertion portion 2.

As a result, an endoscope 1 enabling a bending radius of a bending portion 12 to be reliably and selectively switched to a bending radius R1 or a bending radius R2 for all of bending directions, which are upward, downward, leftward and rightward direction, of the bending portion 12 without an increase in diameter of the insertion portion 2 of the endoscope 1 can be provided.

Another example configuration of the bent shape switching device will be described with reference to FIGS. 9 to 11.

Figure 9:
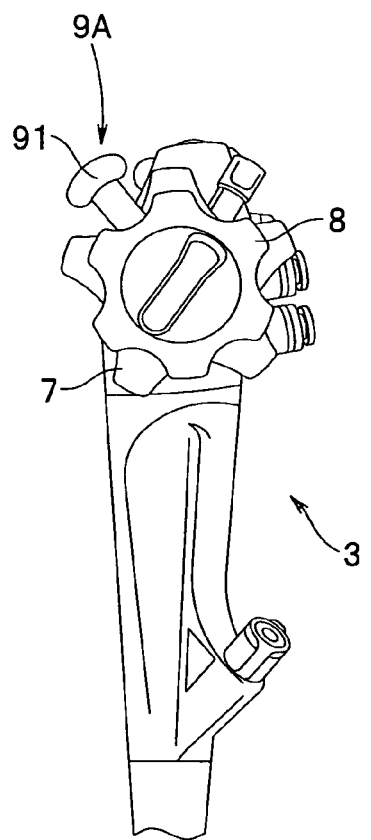
FIGS. 9 to 11 are diagrams illustrating another configuration of a bending portion bent shape switching device.
Figure 11:
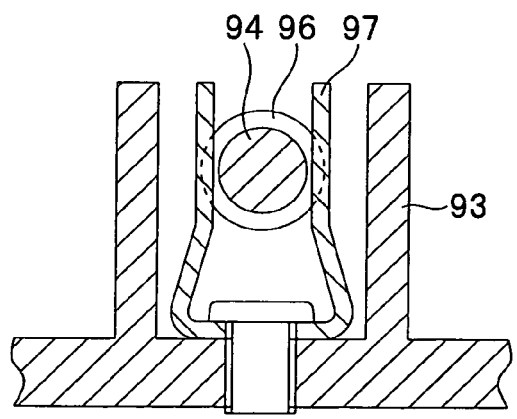
Figure 10:
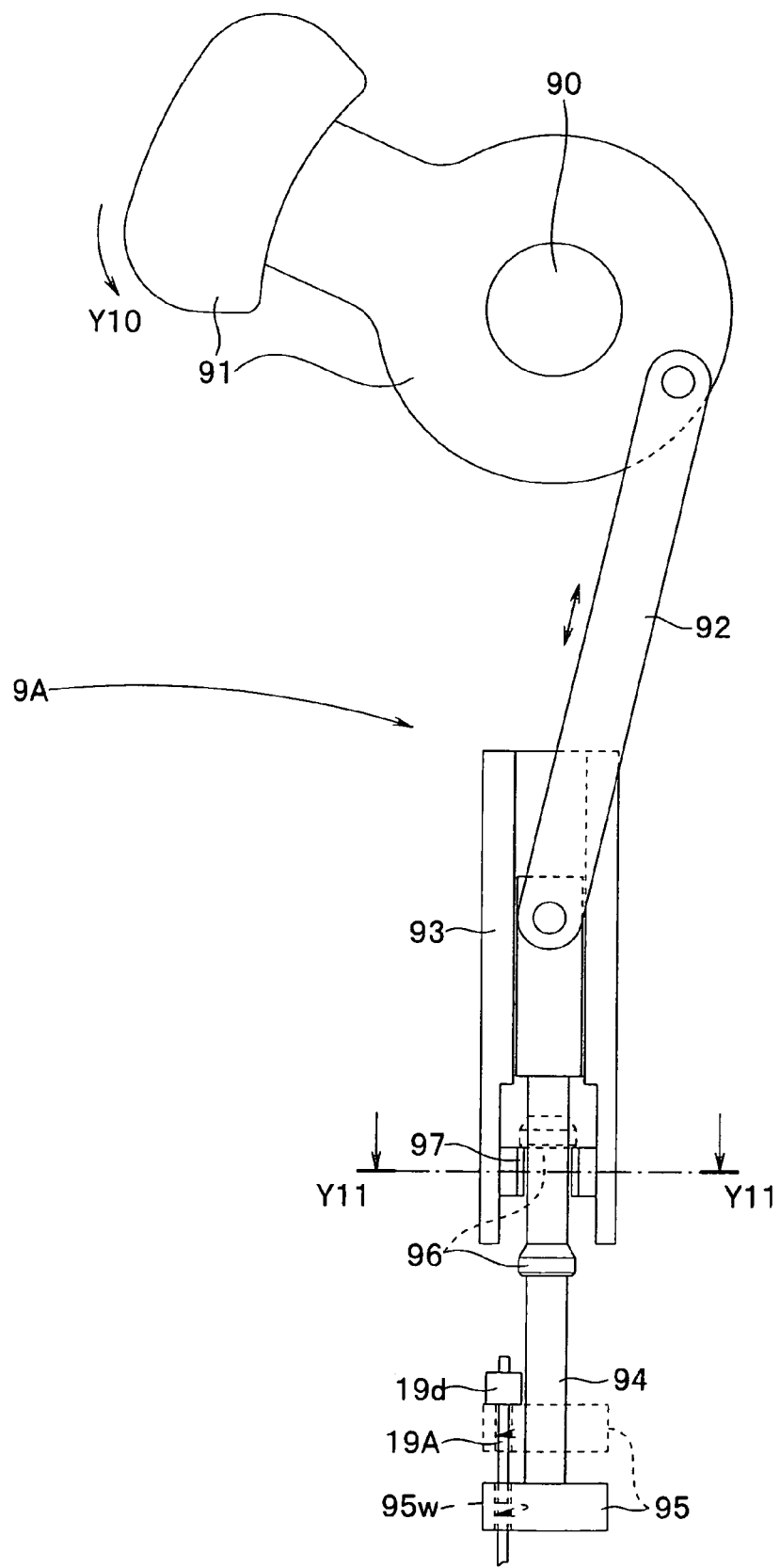

FIG. 9 is a diagram illustrating a lever for pulling bent shape switching wires, which is provided in an operation portion, FIG. 10 is a diagram illustrating a link mechanism provided inside the operation portion, the link mechanism pulling the bent shape switching wires, and FIG. 11 illustrates a cross-section along line Y11-Y11 in FIG. 10.

In the above-described embodiment, the operation ring 9a in the bent shape switching device 9 is rotated along the axis direction of the insertion portion to pull the bent shape switching wires 19A, 19B and 19C, whereby the second bending region 15 is made to enter a hardened state. However, a configuration of the bent shape switching device for hardening the second bending region 15 is not limited to such configuration, and as illustrated in FIG. 9, a configuration in which a bent shape switching lever (hereinafter abbreviated as lever) 91 is provided in the vicinity of a upward/downward knob 7 and a leftward/rightward knob 8 provided at an operation portion 3 may be employed.

With a bent shape switching device 9A, bent shape switching wires 19A, 19B and 19C are pulled/loosened by rotating the lever 91 clockwise or counterclockwise around a later-described axis to switch the second bending region 15 to a hardened state or a bendable state.

As illustrated in FIG. 10, the bent shape switching device 9A includes the lever 91 that rotates clockwise or counterclockwise relative to an operation axis 90. At a predetermined position in the lever 91, a proximal end of a link 92 is pivotably supported. A distal end of the link 92 is pivotably supported at a proximal end of an elongated rod 94 slidably arranged inside a guide member 93. A locking member 95 is fixed to a distal end of the rod 94.

In the locking member 95, axial through holes 95w through which the bent shape switching wires 19A, 19B and 19C are inserted are formed. Furthermore, at a proximal end of each of the bent shape switching wires 19A, 19B and 19C, a stopper 19d is fixedly provided.

FIG. 10 illustrates one of the three bent shape switching wires 19A, 19B and 19C for simplification of the drawings.

When the lever 91 is operated in the arrow Y10 direction by a user, the rod 94 inside the guide member 93 is moved toward the proximal end side by the link 92. Then, in association with the movement of the rod 94, the locking member 95 is moved toward the proximal end side, whereby the stoppers 19d fixedly provided to the bent shape switching wires 19A, 19B and 19C are also moved toward the proximal end side. In other words, the bent shape switching wires 19A, 19B and 19C are simultaneously pulled. As a result, operations and effects similar to those of the above-described bent shape switching device 9 can be provided.

Note that as illustrated in FIG. 10, a projection portion 96 is provided at a position that is made to be distant in advance from a distal end of the rod 94. When the lever 91 is rotated to move the rod 94, for example, toward the proximal end side via the link 92, the projection portion 96 is fixed to a leaf spring 97, which is illustrated in FIG. 11 and provided so as to project on the inner circumferential side of the distal end side of the guide member 93, by means of snap fit as indicated by alternate long and two short dashes lines. Consequently, the position where the rod 94 has moved is fixed, whereby the bent shape switching wired 19A, 19B and 19C are kept in a pulled state.

Note that the present invention is not limited only to the above-described embodiment and various modifications are possible without departing from the scope of the invention.

What is claimed is:

1. An endoscope including an insertion portion including an observation optical system at a distal end portion disposed at a distal end thereof, a bending portion configured to bend in four directions that are a first direction, a second direction, a third direction and a fourth direction, the bending portion being provided so as to be continuous with a proximal end side of the distal end portion, and a flexible tube portion that is soft and has flexibility, the flexible tube portion being provided so as to be continuous with a proximal end side of the bending portion, a plurality of incorporated components being inserted in the insertion portion,
   wherein the bending portion comprises a first bending region including a plurality of first bending pieces pivotably joined so that the first bending region bends in the four directions, the plurality of first bending pieces being included in a distal end side of the bending portion, and a second bending region provided so as to be continuous with a proximal end side of the first bending region, the second bending region including a plurality of second bending pieces pivotably joined so that the second bending region bends in the four directions, the plurality of second bending pieces being included in the proximal end side of the bending portion; and
   wherein the flexible tube portion contains, in an interior space thereof,
   four first guide pipes disposed at respective positions in an inner circumferential face of the flexible tube portion, the positions corresponding to the four directions that are bending directions of the bending portion, the four first guide pipes allowing four bending wires corresponding to the bending directions of the bending portion to be inserted therethrough so that the respective bending wires freely advance/retract, the four bending wires each including a distal end fixed to a distal end of the first bending region and a proximal end fixed to a bending portion operation device provided at an operation portion provided so as to be continuous with a proximal end side of the insertion portion, and
   three second guide pipes disposed at predetermined positions in the inner circumferential face of the flexible tube portion, the three second guide pipes allowing three bent shape switching wires to be inserted therethrough so that the respective bent shape switching wires freely advance/retract, the three bent shape switching wires each including a distal end fixed to a distal end of the second bending region and a proximal end fixed to a bending portion bent shape switching device provided at the operation portion, and the three bent shape switching wires being configured to switch the second bending region to a contracted state by being simultaneously pulled in a direction toward the proximal end by the bending portion bent shape switching device,
   wherein from among the plurality of incorporated components, an incorporated component having a largest outer diameter is located between adjacent two of the first guide pipes in a circumferential direction,
   wherein positions of two second guide pipes of the three second guide pipes in the circumferential direction are set such that one of the two second guide pipes, one of the two first guide pipes, the incorporated component having the largest outer diameter, the other of the two first guide pipes and the other of the two second guide pipes are arranged in this order in the circumferential direction, and
   wherein a position in the circumferential direction where remaining one of the three second guide pipes is located at a position along the inner circumferential face of the flexible tube portion radially opposite the incorporated component having the largest outer diameter.

2. The endoscope according to claim 1, wherein from among the incorporated components, the incorporated component having the largest outer diameter is located at a position to be in contact with the adjacent first guide pipes; and wherein positions in the circumferential direction where the two second guide pipes of the three guide pipes are arranged are located at positions to be in contact with sides of the first guide pipes in contact with the incorporated component having the largest outer diameter, each of the sides being opposite to a side that is in contact with the incorporated component having the largest outer diameter.

3. The endoscope according to claim 1, wherein from among the three bent shape switching wires, tensile strengths of the bent shape switching wires inserted through the second guide pipes located at positions to be in contact with sides of the first guide pipes adjacent to the incorporated component having the largest outer diameter, each of the sides being opposite to the side that is in contact with the incorporated component having the largest outer diameter, are set to be larger than a tensile strength of the bent shape switching wire inserted through the second guide pipe located at the position facing the incorporated component having the largest outer diameter.

4. The endoscope according to claim 1, wherein from among the three bent shape switching wires, diameters of the bent shape switching wires inserted through the second guide pipes located at positions to be in contact with sides of the first guide pipes adjacent to the incorporated component having the largest outer diameter, each of the sides being opposite to the side that is adjacent to the incorporated component having the largest outer diameter, are set to be larger than a diameter of the bent shape switching wire inserted through the second guide pipe located at the position facing the incorporated component having the largest outer diameter.

5. The endoscope according to claim 3, wherein from among the three bent shape switching wires, a tensile strength of a bent shape switching wire that is provided along the inner circumferential face radially opposite of the flexible tube portion radially opposite a bending wire for which a bending angle of the bending portion is set to be largest or that provides bending in a bending direction for which a bending operation is most frequently performed is larger than tensile strengths of the other bent shape switching wires.

* * * * *